United States Patent [19]

Kung

[11] Patent Number: 4,980,467
[45] Date of Patent: Dec. 25, 1990

[54] PREPARATION OF RADIO LABELED HALOGENATED COMPOUNDS

[75] Inventor: Hank F. Kung, Wynnewood, Pa.

[73] Assignee: Trustees of the University of Pennsylvania, Philadelphia, Pa.

[21] Appl. No.: 187,856

[22] Filed: Apr. 29, 1988

[51] Int. Cl.$^5$ .................. C07D 223/02; C07D 207/14
[52] U.S. Cl. ..................................... 540/594; 548/561
[58] Field of Search ................ 540/594, 595; 568/649; 548/561

[56] References Cited

U.S. PATENT DOCUMENTS 3,182,089  5/1965  Wilbert ............................. 568/649
3,338,950  8/1967  Seki et al. .......................... 568/649

OTHER PUBLICATIONS

*Nucl. Med. Biol.*, vol. 15, No. 2, pp. 203–208 (1988).
*Chem. Rev., 1982*, 82, pp. 575–590.
*Tetrahedron*, 20, 43 (1964).
*Tetrahedron*, 20, 2751 (1964).
*J. Nucl. Med.*, 16, 835 (1975).
*J. Radioanal. Chem.*, 65, 163 (1981).
*J. Radioanal. Chem.*, 56, 253 (1980).
*Nucleonics*, 12(2), 65 (1954).
*J. Labeled Compd. Radiopharm.*, 14, 83 (1977).
*J. Med. Chem.*, 6, 428 (1963).
*Acta. Chem. Scand.*, 12, 485 (1958).
Moerlein et al., "No Carrier-Added Radiobromination and Radioiodination of Aromatic Rings Using In Situ Generated Peracetic Acid," *J. Chem. Soc. Perkin Trans.*, 1 (Apr., 1988).
Abstract of a paper by Kung et al., presented at a conference in San Francisco from Jun. 14–17, 1988 entitled "Preparation of $^{123}$IBZM: A Dopamine Receptor Imaging Agent", pub. May, 1988.
Paper by Kung, Mei-Ping and Kung, Hank F., "Peracetic Acid as a Superior Oxidant for Preparation of $[^{123}]$IBZM: A Potential Dopamine D-2 Receptor Imaging Agent," *J. of Labeled Compounds and Radiopharmaceuticals*, Aug., 1988.

*Primary Examiner*—David B. Springer
*Attorney, Agent, or Firm*—Woodcock Washburn Kurtz Mackiewicz & Norris

[57] ABSTRACT

A method for radiolabeling organic compounds is disclosed in which said compounds are contacted with carrier-free radioactive halide ion in the presence of an effective amount of peracetic acid.

6 Claims, No Drawings

PREPARATION OF RADIO LABELED HALOGENATED COMPOUNDS

BACKGROUND OF THE INVENTION

This invention relates to a method for preparing halogenated compounds, and more specifically, for labeling organic compounds with radioactive halogen.

Radioactive isotopes of halogen atoms, especially iodine, have proven to be very useful for labeling both large and small organic molecules. Radioactively labeled compounds have great utility by virtue of the ease with which extremely small amounts of them they may be detected and measured. Radioiodinated compounds are especially useful because the gamma rays which the iodine isotopes emit are detectable directly without the use of a costly and cumbersome scintillation system and because the isotopes have relatively short half-lives.

Radioiodinated compounds have two primary uses. The first, radioimmunoassay, involves the use of antibodies raised against a specific molecule, called an antigen, for its detection in minute amounts. The second major use of radioiodinated compounds is in nuclear medical imaging. Compounds that localize in a particular organ or tissue are used to carry a radiolabel whose emissions are detected outside the body.

An example of a recently developed nuclear medical imaging agents is the compound [$^{125}$I]IBZM, (S)-3-[$^{125}$I]-iodo-2-hydroxy -6-methoxy-N-[(1-ethyl-2-pyrrolidinyl)]methylbenzamide, which has been found to bind specifically to the dopamine D-2 receptor with stereospecificity. Kung, H.F., et al., "Comparison of In Vivo D-2 Dopamine Receptor Binding of IBZM and NMSP in Rat Brain," *Nucl. Med. Biol.*, Vol. 15, No. 2, pp. 203–208, 1988. A related imaging agent is the compound [$^{125}$I]IBZP, (R)-(+)-8-[$^{125}$I]-iodo-2,3,4,5-tetrahydro-3-methyl-5-phenol-1-H-3-benzazepine-7ol. Kung, H.F. et al., *Op. cit.*, pp 187–193. The agent IBZP is specific for Dopamine D-1 receptor. Since $^{125}$I-isotopes are generally not useful for labelling imaging agents, by virtue of their relatively long half-lives (60 days) and low gamma-emission (30–65 Kev), it is proposed that $^{123}$I-labelled BZM or BZP ($^{123}$I has a half life of 13 hours, gamma energy 159ke V) would be useful as an imaging agent for the investigation of dopamine D-1 and D-2 receptors in humans, and, thus, as a tool for studying the biochemistry and metabolism of the living human brain.

For $^{123}$I-labelled agents to be practically useful, there must be a method for quickly, conveniently and efficiently labelling the agents with the radioactive isotope. The short half-life of the isotope is beneficial from the standpoint of safety to the patient to whom it will be administered but also dictates that the labelling procedure be one which can be quickly accomplished. The labelling procedure should also be one which will lead to a labeled molecule of high specific activity. Specific activity is a measure of the radioactivity of a labeled molecule, maximum specific activity being obtained when each molecule in the preparation is radiolabeled.

Methods for labelling organic molecules with radioactive iodine have been reviewed by Seevers and Counsell, "Radioiodination Techniques for Small Organic Molecules," *Chem. Rev.*, 1982, 82, 575–590. As discussed therein, the earliest methods of radiolabeling involved application of methods known in the art for iodinating phenols with stable iodine. Radioactive molecular iodine was the most commonly employed labeling reagent; however, since radioactive iodine is usually available as sodium iodide, a means of oxidation had to be employed to obtain radioactive molecular iodine. Agents such as ammonium persulfate, hydrogen peroxide, ferric sulfate or an iodide/iodate system were used for oxidation prior to radiolabeling. There are, however, a number of disadvantages to the use cf molecular iodine for radiolabeling. First, since half of the label ends up as radioiodide, the maximum possible radiochemical yield is only 50%. Second, the prior oxidation step involves some loss of radioactivity and increased radiation exposure to the operator. Third, the volatility of molecular iodine greatly magnifies the hazards of the labeling procedure.

Although not related to labeling with radioactive isotopes, it should be noted that the nonradioactive iodination of benzene and phenyl compounds with a mixture of peroxyacetic acid and molecular iodine have been reported in excellent chemical yield. Ogata, Y. and Nakajima, K., "Iodination of Aromatic Compounds with a Mixture of Peroxyacetic Acid and Iodine," *Tetrahedron*, 20, 43 (1964), and "Studies on the Iodination of Aromatic Compounds by a Mixture of Peroxyacetic Acid and Iodine," *Tetrahedron*, 20, 2751 (1964). To the knowledge of the inventor, no reference has suggested the use of peracetic acid oxidizing agent when the source of iodine was iodide ion rather than molecular iodine.

To avoid the disadvantages associated with iodination methods using molecular iodine, techniques using radioactive iodide were developed. The most widely used technique uses chloramine T as an oxidizing agent. The active iodinating moiety is generated by oxidizing $I^-$ to $I^+$, by which the electrophilic oxidative iodination of phenols and other activated aromatic rings systems take place. Meyers, J., et al., *J. Nucl. Med.*, 16, 835 (1975); Baldwin, R.M., et al., *J. Radioanal. Chem.*, 65, 163 (1981). The chloramine T technique, however, also suffers certain disadvantages. One problem is that the compound to be labeled is exposed to harsh oxidizing conditions which can lead to undesirable side reactions. Another problem is that radiolabeling reactions involving chloramine-T usually require a fine control of the molar ratio of oxidant and substrate and of the reaction time. Finally, the chloramine-T reaction often produces radioactive and non-radioactive side products which must be separated from the desired iodinated compounds. A number of other oxidants for radioactive iodination have been reported, and these include hydrogen peroxide (H, -J. Machulla, M. Marsman and K. Dutschka, *J. Radioanal. Chem.*, 56, 253 (1980); ammonium persulfate (R.C. Gilmore, Jr., M.C. Robbins and A.F. Reid, *Nucleonics*, 12(2), 65 (1954); nitric acid (W.G. Keough and K.G. Hofer, *J. Labeled Comod. Radiopharm.*, 14, 83 (1977); iodate (P.K. Chang and A.D. Welch, *J. Med. Chem.*, 6, 428 (1963); and chlorine water (G. Ehrensvard, J. Liwekvist, K. Mosbach and P. Fritzson, *Acta. Chem. Scand.*, 12, 485 (1958). However, there remains a need for a method for quickly, conveniently and efficiently labelling organic molecules with radioactive halogens such as $^{123}$I.

SUMMARY OF THE INVENTION

A method for radiolabeling organic molecules has now been found which overcomes many of the disadvantages associated with the aforementioned prior art processes. According to this method, an organic compound having an aromatic group may be radiolabeled by contacting said compound with carrier-free radioactive halide ion in the presence of an effective amount of peracetic acid. In the preferred embodiment, the halide ion is a radioactive iodide, such as $^{125}I-$, $^{123}I-$ or $^{131}I-$.

DETAILED DESCRIPTION OF THE INVENTION

The term "carrier free" as used in describing this invention is intended to mean a labeled compound to which no stable halogen has been added. Thus, a carrier free $^{123}I-$ would have no iodine-127 added.

The term "activated aromatic group" as used in describing this invention is intended to mean an aromatic group which is more reactive to electrophilic substitution than benzene. Generally, benzene rings substituted with at least one electron-donating group such as but not limited to $-NH_2$, $-NHR$, $-NR_2$, $-OH$, $-OR$, $-NHC(O)R$, $-C_6H_5$ or alkyl are "activated" groups. Aromatic groups having heteroatoms, such as but not limited to furans, thiophenes and pyrroles, are also "activated" aromatic groups.

In carrying out the method of this invention, the peracetic acid oxidizing agent is preferably added to an acidic solution of the compound to be labeled and the radioactive halide ion, e.g., $Na^{123}I$, $Na^{125}I$ or $Na^{131}I$. The compound to be labeled may be any organic compound having an aromatic group and preferably contains an activated aromatic group. Other radioactive halides which may be used include but are not limited to $^{77}Br-$, $^{76}Br-$, $^{75}Br-$, $^{79}Br-$ and $^{82}Br-$. Various aqueous solutions can be used, such as but rot limited to sodium phosphate, ammonium acetate and hydrochloric acid. The optimum pH value is in the range of about 2.0 to 4.0. The reaction proceeds rapidly at room temperature. Although higher or lower temperatures can be used if desired, the thermal stability of the organic compound being labeled will influence the labelling yield. Also, although the reaction proceeds rapidly at room temperature, e.g., within two to five minutes, longer reaction times do not lead to any significant amount of undesired product.

The effective amount of oxidizing agent is at least that amount needed to react with the radioactive halide present to form an electrophilic halide species which will attack the activated aromatic ring of the compound to be labeled. Since such small quantities of radioactive halide ion are used, the molar amount of oxidizing agent will generally far exceed the molar amount of halide. Tests indicate that the optimal ratio of peracetic acid to halide ion is generally in the range of about $10^3$ to $10^6$; however, the optimal ratio will vary from isotope to isotope.

To better illustrate the method of this invention, it has been further illustrated in comparison with other halogenation methods in Example 1. Results are presented in Table 1.

EXAMPLE

Reagents, Solvents, Equipment:

BZM was prepared by a method described previously. Kung et al., supra. Sodium [$^{125}I$] iodide was obtained from Amersham in a non-carrier added form (specific activity greater than 17Ci/mg, 2200 Ci/mmmole). Chloramine-T hydrate, peracetic acid (32 wt % solution in dilute acetic acid containing 17.4% water), sodium persulfate (98%+) and 3-chloropeoxybenzoic acid (80-85%) were purchased from Aldrich Chemicals. The 3-chloropeoxybenzoic acid was repurified by washing with phosphate buffer (pH 7.4) and dried under vacuum to reach greater than 95% purity. Peracetic acid was diluted 1/10 and 1/20 with water to make up a Solution A (3.2 wt. %) and a Solution B (1.6 wt. %). Hydrogen peroxide (30%) was obtained from Fisher Scientific. Ethyl acetate and acetonitrile were HPLC grade and purchased from J.T. Baker. All other chemicals were reagent grade and purchased commercially. The radiochemical purity of the desired compound [$^{125}I$]IBZM, labeled using the different oxidizing agents, was analyzed by HPLC using a reverse-phase column (PRP-1 column, Hamilton) and an acetonitrile-3,3-dimethyl glutaric acid (pH 7.0) solvent system (82:18).

Radiolabeling

The oxidizing agent was added to a mixture of BZM (50 μg, 1 mg/ml EtOH), sodium [$^{125}I$] iodide (10 ul, 20-50 μCi) and buffer (sodium phosphate, pH 3.0 or ammonium acetate, pH 4.0, 0.3 ml) or hydrochloride (0.1N, 0.1 ml) solution in a sealed vial. The reaction time was allowed to proceed at room temperature, 65° C. or 100° C. for the indicated time period depending on the individual oxidizing agent. The reaction was terminated by addition of sodium bisulfite (0.1 ml, 50 mg/ml) and neutralized with saturated sodium bicarbonate (0.5-1.0 ml). The product was extracted with ethyl acetate (1 ml×3). The combine organic layers were dried by passing through an anhydrous sodium sulfate column (0.2 cm×5 cm). The labeling yield with individual oxidizing agent was determined by measuring the radioactivity associated with the ethyl acetate layer and the aqueous layer individually. The organic solution was evaporated under a stream of nitrogen and the residue was dissolved in absolute ethanol (10-20μl). The labeled product was analyzed by HPLC for radiochemical purity determination. The percent of purity was calculated by dividing the total counts of the peak with a retention time of 15 minutes (corresponding to IBZM) to total counts. The optimal conditions and results determined for each oxidant are presented in Table 1.

TABLE 1

OPTIMUM IODINATING CONDITIONS OF BZM* WITH VARIOUS OXIDIZING AGENTS

| Oxidizing Agt. | Amount | Buffer | Temp. | Rx. time (min) | Labeling yield % | Radiochem purity % |
|---|---|---|---|---|---|---|
| chloramine-T | 50 μg | Na-phosp pH 3.0 | Room | 1.5 | 80-90 | 90-95 |
| hydrogen peroxide | 100 μl 3% | Na-phosp pH 3.0 | 100° C. | 30 | 85-90 | 92-95 |
| peracetic | 100 μl Soln. A | NH₄OAc pH 4.0 | Room | 2 | 90-95 | 93-95 |
| chloropeoxy-benzoic acid | 50 μg | Na-phosp pH 3.0 | 65° C. | 30 | 70-79 | 85-90 |

TABLE 1-continued

OPTIMUM IODINATING CONDITIONS OF BZM*
WITH VARIOUS OXIDIZING AGENTS

| Oxidizing Agt. | Amount | Buffer | Temp. | Rx. time (min) | Labeling yield % | Radiochem purity % |
|---|---|---|---|---|---|---|
| sodium | 100 mg | Na-phosp pH 3.0 | 65° C. | 30 | 35–40 | 65–68 |

*BZM: 50 µg

Results

The labeled products obtained were compared with chemically pure nonradioactive IBMZ on HPLC using simultaneous U.V. and radioactivity detection and were determined to be the desired products based on their elution profiles.

The labeling reaction of BZM with chloramine-T was instantaneous at room temperature, with the optimal conditions for the labeling at pH 3.0 with BZM (50 µg) to chloramine-T (50 µg) in 0.3 ml buffer. The total labeling yield as high as 90% could be obtained, but the pH of the reaction solution and the concentration of the chloramine-T showed significant effect on the labeling yield. Due to the harsh oxidizing condition to which the compound to be labeled (BZM) is exposed in the chloramine-T method, the reaction time was optimally kept short (1.5 min) in order to avoid any possible undesirable side products.

BZM labeling using hydrogen peroxide as oxidant required a high temperature (100° C.) and prolonged reaction time (20–30 min). Nonetheless, a good labeling yield and high radiochemical purity were obtained.

The labeling of BZM using sodium persulfate as oxidant did not proceed well, and the reaction gave some undesired product. Due to the instability of sodium persulfate in aqueous solution and elevated temperature, this oxidant is a poor candidate for radioiodination.

Tests indicated that 3-chloropeoxybenzoic acid was a fairly good oxidant for the labeling of BZM. An elevated temperature (65° C.) was required, but labeling yield (70–79%) and product purity (85–90%) were fairly good. Although the iodide/oxidant/BZM ratios indicated in Table 1 represent the optimal ratios of those reactants, good results should be obtained if the ratios of the reactants is varied by a range of two in either direction.

Of all the oxidants studied, peracetic acid was by far the best for radiolabeling of BZM. Very high yield and product purity were obtained in a short reaction time at room temperature. Thus, the following advantages are associated with the use of peracetic acid:

(1) The reaction time required with peracetic acid is short. Iodination can be completed within two to five minutes. Prolonged reaction time does not lead to any significant amount of undesired product.

(2) The reaction proceeds rapidly at room temperature. Thus, any side reaction or instability of the starting material caused by raising the temperature during the iodination reaction can be avoided.

(3) The radiolabeling yield is excellent with peracetic acid (90–93%). The radiochemical purity approaches 95%. Use of this oxidant results in the production of fewer undesired side products than use of any of the other tested oxidants.

EXAMPLE 2

Peracetic acid has also been examined as an alternative oxidizing agent for the preparation of [$^{125}$I]IBZP. Data for experiments run using peracetic acid and, by comparison, chloramine-T, are presented in Table 2. Interestingly, the optimal ratio of oxidant to substrate (i.e., peracetic acid to BZP) is lower than that for IBZM preparation, reflecting that IBZP is more sensitive than IBZM toward this particular oxidant. The reaction time for the radioiodination of BZP should also be kept short to avoid undesired product. The preliminary results indicated that [$^{125}$I]IBZP prepared with peracetic acid showed a labeling yield comparable to that obtained with chloramine-T. The radiochemical purity obtained with peracetic acid was superior to that obtained with chloramine-T.

TABLE 2

RADIOIODINATION OF BZP*

| Oxidizing Agt. | Amount | Buffer | Temp. | Rx. time (min) | Labeling yield % | Radiochem purity % |
|---|---|---|---|---|---|---|
| Chloramine-T | 50 µg | Na-phosp pH 3.0 | Room | 1.5 | 77 | 84 |
| Peracetic acid | 100 µl Soln. A | Na-phosp pH 3.0 | Room | 5.0 | 76 | 0 |
| " | 50 µl Soln. A | Na phosp pH 3.0 | " | 2.0 | 88 | 67 |
| " | 50 µl Soln. B | Na-phosp pH 3.0 | " | 2.0 | 75 | 93 |

*BZP: 50 µg

What is claimed is:

1. In a method for radiolabeling an organic comound having at least one aromatic or heteroaromatic group with carrier-free radioactive iodide, chloride or bromide, in the presence of an oxidizing agent in an acidic buffered solution, wherein the improvement lies in utilizing peracetic acid as said oxidizing agent.

2. A method for radiolabelling a compound selected from the group consisting of (S)-2-hydroxy-6-methoxy-N-methylbenzamide and (R)-(+)-2,3,4,5-tetrahydro-3-methyl -5-phenol-1-H-3-benzazepine-7-ol comprising contacting said compound with carrier-free radioactive halide selected from the group consisting of iodide, chloride and bromide in the presence of a buffer solution with an acidic pH of about 2.0 to 4.0 and an effective oxidizing amount of peracetic acid.

3. The method of claim 2 where said radioactive halide is iodide.

4. The method of claim 2 wherein said buffer solution is selected from the group consisting of solutions of sodium phosphate/hydrochloric acid and ammonium acetate/hydrochloric acid.

5. The method of claim 2 where said compound, halide and peracetic acid are contacted at room temperature.

6. The method of claim 2 wherein said halide is iodide, said buffer solution and is selected from the group consisting of solutions of sodium phosphate/hydrochloric acid and ammonium acetate/hydrochloric acid.

* * * * *

UNITED STATES PATENT AND TRADEMARK OFFICE
CERTIFICATE OF CORRECTION

PATENT NO. : 4,980,467
DATED : December 25, 1990
INVENTOR(S) : KUNG

It is certified that error appears in the above-identified patent and that said Letters Patent is hereby corrected as shown below:

Column 1, line 37: "...H-3-benzazepine-7ol." should be --...H-3-benzazepine-7-ol.--

Column 1, line 43: "...BZP($^{123}$I..." should be --...BZP($^{123}$I...--

Column 2, line 55: "Comod." should be --Compd.--

Column 3, line 33: "rot" should be --not--

Column 4, line 43: "combine" should be --combined--

Column 5, line 14: "IBMZ" should be --IBZM--

Column 6, line 62: After "N-" and before "methylbenzamide", please insert --[(1-ethyl-2-pyrrolidinyl)]--

Signed and Sealed this

Twenty-third Day of June, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,980,467

DATED : December 25, 1990

INVENTOR(S) : Hank F. Kung

It is certified that error appears in the above-identified patent and that said Letters Patent is hereby corrected as shown below:

Column 1, line 4, after BACKGROUND OF THE INVENTION, please insert "Portions of this invention were supported by grants from NIH NS-24538. The United States Government may have rights in this invention."

Signed and Sealed this

Eighteenth Day of October, 1994

Attest:

BRUCE LEHMAN

Attesting Officer

Commissioner of Patents and Trademarks